(12) United States Patent
Knapp

(10) Patent No.: US 7,907,991 B2
(45) Date of Patent: Mar. 15, 2011

(54) SYSTEM AND METHOD FOR MARKING BODY CAVITIES

(75) Inventor: Tracey E. Knapp, Lawrenceville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 996 days.

(21) Appl. No.: 11/070,813

(22) Filed: Mar. 2, 2005

(65) Prior Publication Data
US 2006/0200024 A1 Sep. 7, 2006

(51) Int. Cl.
*A61M 25/00* (2006.01)
*A61B 6/00* (2006.01)
*A61B 5/05* (2006.01)

(52) U.S. Cl. .................. 600/433; 600/478; 600/411

(58) Field of Classification Search .......... 600/431–435; 604/113, 264, 523; 424/65
See application file for complete search history.

(56) References Cited

U.S. PATENT DOCUMENTS

| | | | |
|---|---|---|---|
| 4,485,812 A | 12/1984 | Harada et al. | |
| 4,802,461 A * | 2/1989 | Cho | 600/108 |
| 4,807,626 A * | 2/1989 | McGirr | 606/127 |
| 4,945,895 A * | 8/1990 | Takai et al. | 600/104 |
| 5,195,964 A * | 3/1993 | Kletzky et al. | 604/523 |
| 5,455,026 A * | 10/1995 | Bahr et al. | 424/65 |
| 6,427,081 B1 | 7/2002 | Burbank et al. | |
| 6,544,227 B2 * | 4/2003 | Sahatjian et al. | 604/113 |
| 6,565,530 B2 * | 5/2003 | Sahatjian et al. | 604/113 |
| 6,589,998 B1 | 7/2003 | Bianchi et al. | |
| 6,663,594 B2 * | 12/2003 | Sahatjian et al. | 604/113 |
| 7,137,966 B2 * | 11/2006 | Sahatjian et al. | 604/113 |
| 7,204,826 B2 * | 4/2007 | Tremaglio et al. | 604/164.12 |
| 2003/0023142 A1 * | 1/2003 | Grabover et al. | 600/143 |
| 2003/0144594 A1 * | 7/2003 | Gellman | 600/466 |
| 2005/0065483 A1 * | 3/2005 | Nakao | 604/264 |
| 2008/0058836 A1 * | 3/2008 | Moll et al. | 606/130 |
| 2009/0198250 A1 * | 8/2009 | Kear | 606/127 |

FOREIGN PATENT DOCUMENTS
EP 1491147 A 12/2004

OTHER PUBLICATIONS

Dec. 22, 2008, European Examination Report for application No. 06736662.5 filed on Oct. 26, 2007.
Apr. 7, 2006 International Search Report from Application PCT/US2006/007381.
Feb. 9, 2007 Written Opinion of the International Searching Authority from Application No. PCT/US2006/07381.

* cited by examiner

*Primary Examiner* — Long V Le
*Assistant Examiner* — Angela M Hoffa
(74) *Attorney, Agent, or Firm* — Rutan & Tucker, LLP

(57) ABSTRACT

Systems and methods for marking a body cavity. In one embodiment, a system includes means for inspecting a body cavity, and means for visibly marking the body cavity so as to convey visual information regarding the body cavity. In one embodiment, a method includes inspecting a body cavity and marking the body cavity with a marking material to provide a visual indication regarding the cavity. In one embodiment, a marking material for marking a body cavity includes a radiopaque contrast agent that is viewable through fluoroscopy and a colored dye that is viewable using an internal viewing device.

12 Claims, 9 Drawing Sheets

SYSTEM AND METHOD FOR MARKING BODY CAVITIES

BACKGROUND

Surgeons are often called upon to inspect internal body cavities to diagnose or remedy a medical condition. For example, a surgeon may inspect the calices of a patient's kidney to search for and remove kidney stones.

In the case of kidney inspection and stone removal, the surgeon may need to inspect each of multiple calices of the kidney. FIG. 1 illustrates a typical kidney 10 that is representative of a kidney that a surgeon may need to inspect. As is shown in FIG. 1, the kidney 10 includes an outer capsule 12 that surrounds a renal cortex 14 in which a plurality of minor calices 16 are formed. Each of the minor calices 16 may extend from a major calyx 18 that, in turn, extends from the renal pelvis 20. The renal pelvis 20 is connected to the ureteropelvic junction 22, which leads down to the ureter 24.

To inspect the kidney 10, the surgeon will normally insert a viewing device, such as an endoscope, into each of the calices 16 of the kidney 10 to enable visual inspection of each calyx for stones. Such a viewing device may be inserted into the kidney via the urinary tract. Fluoroscopy may also be used during such a procedure to aid the surgeon in positioning the viewing device in the desired portion of the kidney 10.

It is common for surgeons to use a top-to-bottom approach when inspecting the kidney 10. In such a procedure, the surgeon checks a first calyx 16, determines whether it contains any stones, and, assuming it does not, checks the next calyx. When a stone is discovered, it is fragmented, if necessary, and removed from the calyx 16 using a retrieval device. This process continues from the top 26 of the kidney 10 to the bottom 28 of the kidney until each calyx 16 has been inspected and every stone or stone fragment has been removed. During the process, the surgeon or the surgical staff tracks which calices 16 have been inspected in an effort to ensure that each calyx is checked.

Because there may be many different calices 16 to inspect and because the position of the viewing device can only be inferentially determined from the images captured by the viewing device and any captured fluoroscopic images, it is often difficult for the surgeon to know with any certainty whether a given calyx has or has not been inspected. As a result, the surgeon may revisit one or more calices one or more times to ensure that it has been checked and does not contain any stones. This "double-checking" lengthens the time required to complete the procedure, thereby increasing risk and/or discomfort to the patient.

Even in cases in which the surgeon and staff are careful in keeping track of which calices 16 have been inspected, it is possible for them to make a mistake that results in one or more calices not being inspected. In such a case, one or more stones or stone fragments may remain which can act as seeds for further stone formation.

In cases in which a stone must be fractured before being removed, for instance if the stone is too large to be removed as a single piece, lithotripsy may be performed to break the stone into smaller fragments. When lithotripsy is performed, it is possible for a stone fragment to be propelled into a calyx 16 that has already been checked. If this happens, one or more stones or stone fragments may remain which, again, can act as seeds for further stone formation.

SUMMARY

Disclosed are systems and methods for marking a body cavity. In one embodiment, a system includes means for inspecting a body cavity, and means for visibly marking the body cavity so as to convey visual information regarding the body cavity.

In one embodiment, a method includes inspecting a body cavity, and marking the body cavity with a marking material to provide a visual indication regarding the cavity.

In one embodiment, a marking material for marking a body cavity includes a radiopaque contrast agent that is viewable through fluoroscopy, and a colored dye that is viewable using an internal viewing device.

BRIEF DESCRIPTION OF THE DRAWINGS

The disclosed system and method can be better understood with reference to the following drawings. The components in the drawings are not necessarily to scale.

DETAILED DESCRIPTION

Figure 1:
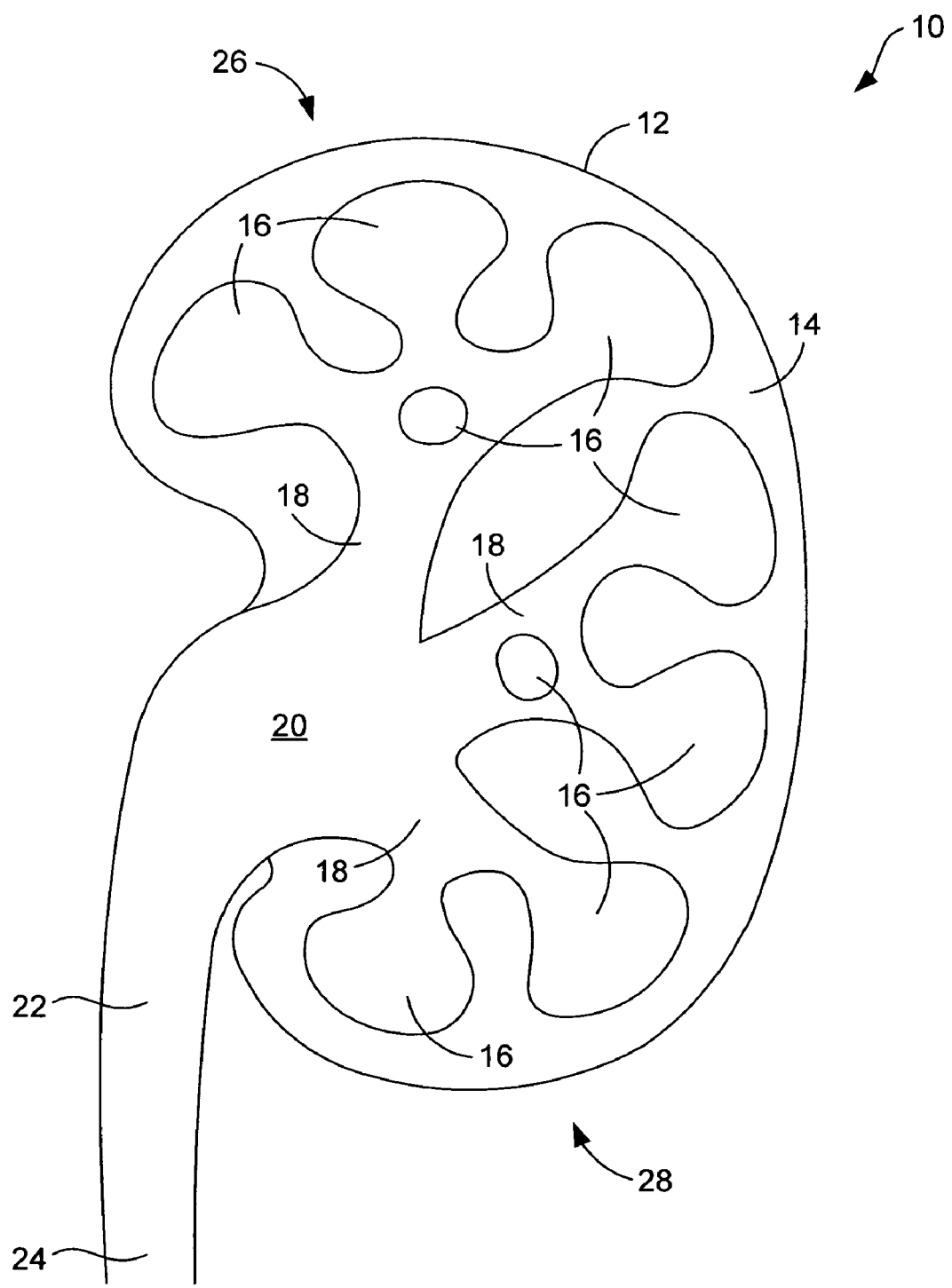
FIG. 1 is a schematic cross-sectional view of a kidney.

As is described in the foregoing, it can be difficult to keep track of which of multiple body cavities have or have not been inspected during a surgical procedure. As is discussed in the following, however, the progress of such inspection can be clearly indicated using a marking material. By way of example, such a marking material can be used to mark one or more cavities that have already been inspected. Alternatively, a marking material can be used to mark one or more cavities of interest, for example that contain an object to be removed. In a further alternative, a first type of marking material can be used to mark cavities of a first type (e.g., that contain objects to be removed) and a second type of marking material can be used to mark cavities of a second type (e.g., that contain no objects to be removed). The marking material contains a marking substance that can be viewed with a viewing device and/or that can be viewed fluoroscopically. In the former case, the marking substance may comprise a dye. In the latter case, the marking substance may comprise a contrast agent.

Referring now to the drawings, in which like reference numerals identify corresponding components, FIGS. 2A-E illustrate various steps in an embodiment of a method for inspecting a plurality of internal body cavities. In the example of FIGS. 2A-2E, the body cavities comprise calices of a kidney that are to be inspected for kidney stones. Although a kidney application is shown in the figures and is described in detail herein for purposes of example, the systems and methods of this disclosure can be applied to other internal body cavities. Therefore, the present disclosure is intended to cover applications beyond kidney inspection and stone removal.

Figure 2A:
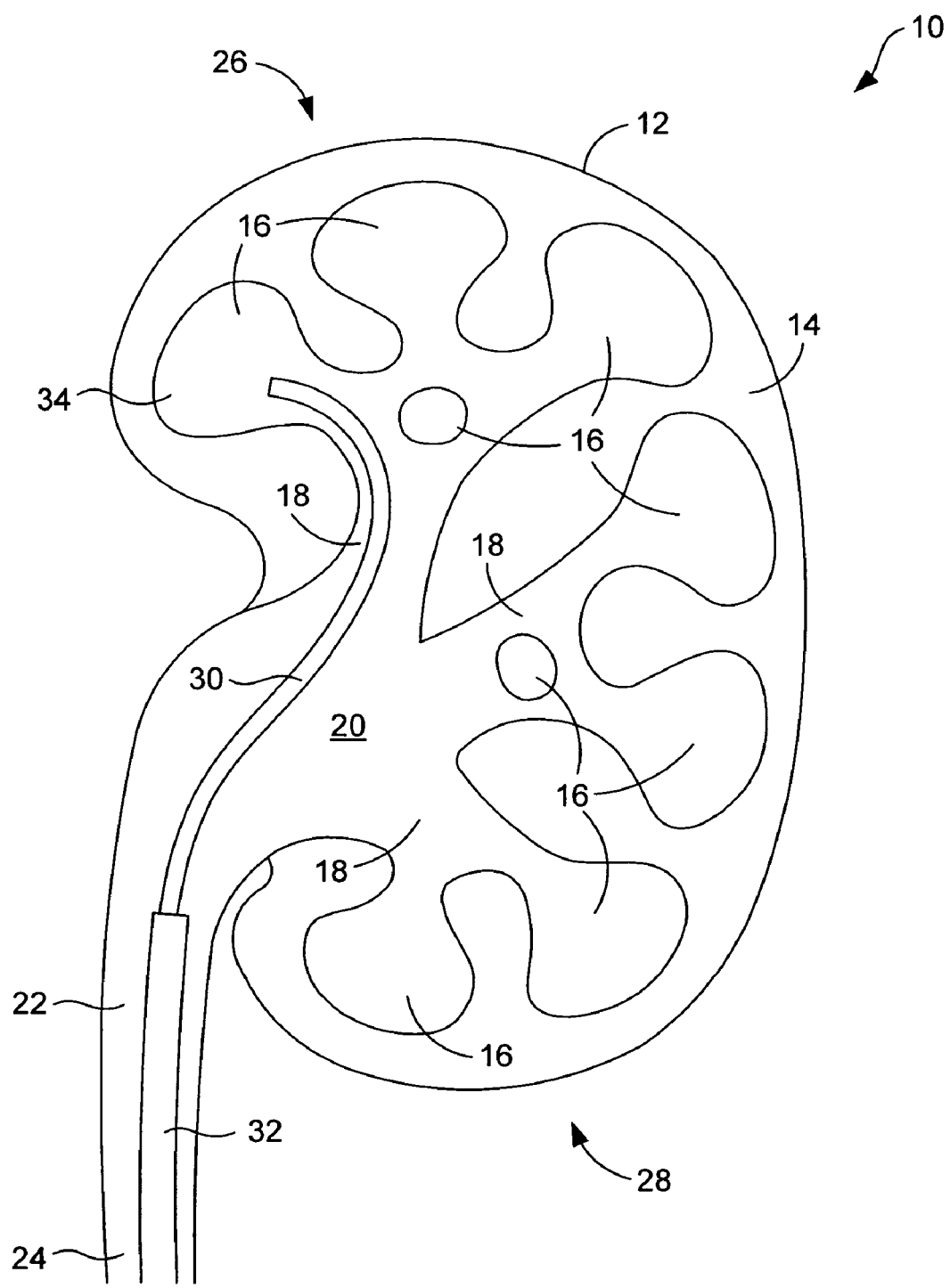
FIG. 2A is a schematic cross-sectional view of a kidney, illustrating inspection of a first calyx using a viewing device.

Beginning with FIG. 2A, illustrated is the kidney 10 first described in relation to FIG. 1. As is described above, the kidney 10 comprises a plurality of calices 16 that may comprise kidney stones that are to be removed (none visible in the view of FIG. 2A). While the bodies of some of the calices 16 are visible in FIG. 2A, only the openings of other calices are visible (indicated by circles in FIGS. 2A-2E).

As is illustrated in FIG. 2A, an internal viewing device 30 has been inserted into the kidney 10 via the ureter 24. By way of example, the viewing device 30 comprises a ureteroscope that has been inserted through a ureteral access sheath 32 that has been inserted into the urinary tract via the external meatus. Although use of an access sheath 32 is depicted in FIG. 2A, the viewing device 30 could, alternatively, be inserted through the urinary tract without the access sheath. Use of the access sheath 32, however, simplifies insertion and removal of the viewing device 30, particularly in cases in which the viewing device must be repeatedly inserted and removed, as when removing multiple stone fragments. In alternative embodiments, the viewing device 30 can be introduced into the kidney 10 using other methods, for instance percutaneously.

With further reference to FIG. 2A, the viewing device 30 has been maneuvered into a first calyx 34 of the upper portion of the kidney 10. That calyx 34 may, for example, be a suitable calyx to start with in a top-to-bottom inspection procedure, such as that described in the foregoing. As is shown in FIG. 2A, the calyx 34 is clear of any stones or other objects that would require removal. Because of this, no further action is required in relation to the calyx 34, and the surgeon may move on to the next calyx 16 of the kidney 10.

Figure 2B:
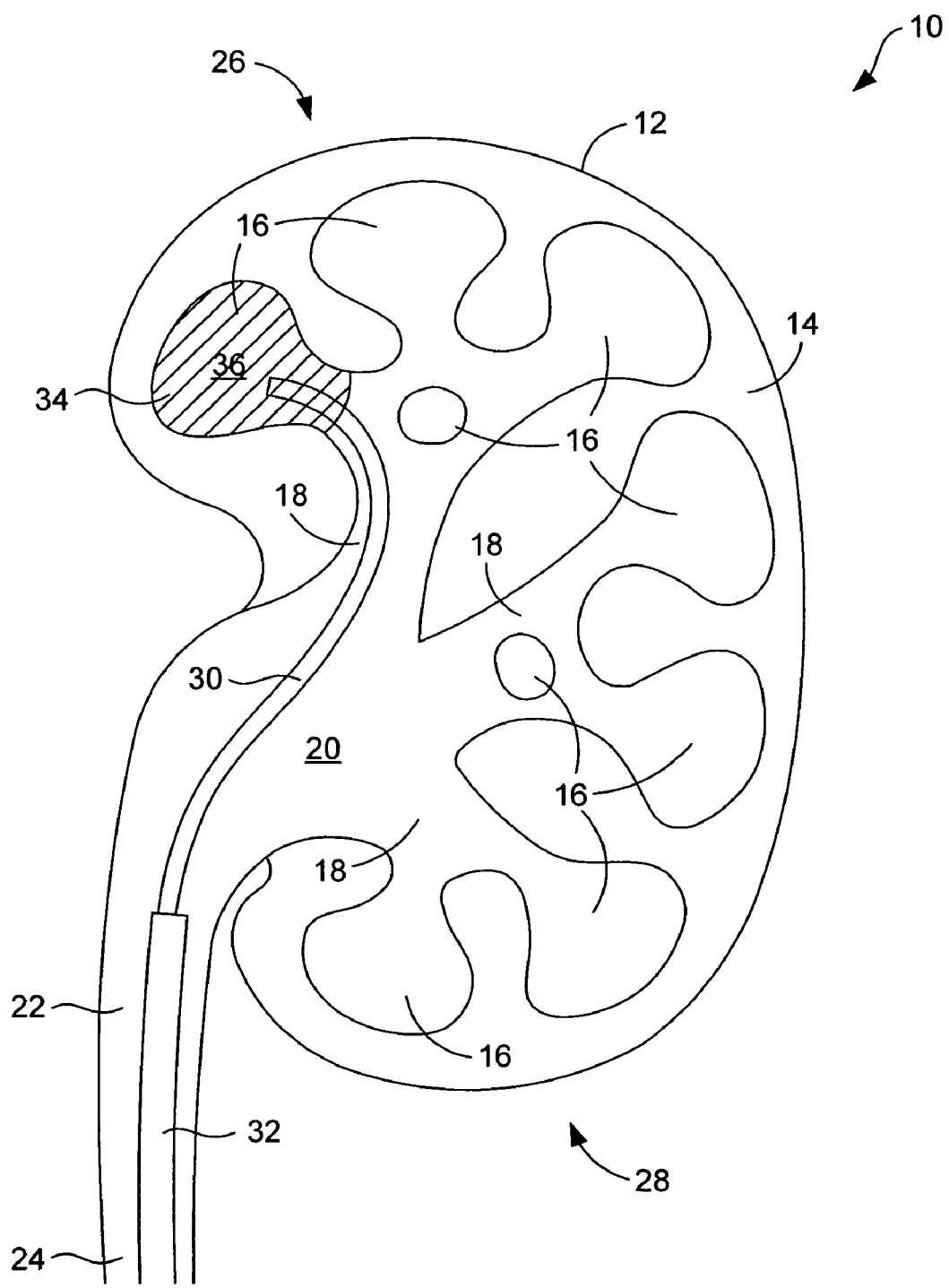
FIG. 2B is a schematic cross-sectional view of a kidney, illustrating marking the first calyx with a marking material.

As is described above, it can be difficult for a surgeon or the surgical staff to keep track of which calices 16 have or have not been inspected. To avoid this problem, the surgeon can mark the calyx 34 prior to moving on to the next calyx 16. By marking the calyx 34 in this manner, the surgeon can readily determine that he or she has already inspected that calyx and understand that no further inspection of the calyx is necessary. In some embodiments, marking can be achieved by filling the calyx 34 with a marking material. Such a procedure is illustrated in FIG. 2B. As is indicated in that figure, the calyx 34 has been filled with a marking material 36. Although the entire calyx 16 is shown filled with that marking material 36, the calyx (or other cavity) could be marked by filling only a portion of the calyx with the marking material. For example, the marking material 36 could be used to fill just the entrance to the calyx 34, if desired.

The marking material 36 can be deposited using various different devices and techniques. In some embodiments, the marking material 36 is injected into the calyx 34 (or other cavity) using a working or irrigation channel of the viewing device 30. In other embodiments, the marking material 36 is delivered using a separate catheter that is inserted through the urinary tract (not shown). In still further embodiments, the marking material 36 is percutaneously injected into the desired site using an external injection device, such as a syringe.

Irrespective of the manner in which the marking material 36 is deposited, the marking material contains a marking substance that is visible using one or both of the viewing device and fluoroscopy. In some embodiments, the marking material 36 comprises one or more dyes that enable the surgeon to readily identify the marking material when viewing the kidney interior using the viewing device 30. Suitable dyes include, for example, methylene dyes, such as methylene blue and methylene red. When such a dye is used, the surgeon will be able to readily determine that the calyx 34 has already been inspected upon later returning to that area of the kidney 10.

In some embodiments, the marking material 36 further or alternatively includes a contrast agent that enables identification of the marking material, and the cavity in which it is placed, through fluoroscopy. The term "contrast agent" refers to any radiopaque material capable of being fluoroscopically monitored. The contrast agent can be either water soluble or water insoluble. Examples of water soluble contrast agents include metrizamide, iopamidol, iothalamate sodium, iodomide sodium, and meglumine. Examples of water insoluble contrast agents include tantalum, tantalum oxide and barium sulfate, each of which is commercially available in the proper form for in vivo use. Other water insoluble contrast agents include gold, tungsten and platinum. As with the dye, the contrast agent assists the surgeon in determining which calices 16 (or other cavities) have already been inspected.

In some preferred embodiments, the marking material 36 is in liquid form prior to deposition, but forms a gel after or during deposition. In some embodiments, the marking material 36 can be a temperature-sensitive material that is in liquid form below normal body temperature, but that forms a gel at or above body temperature. Such materials include lower critical solution temperature materials, such as polyoxyethylene-polyoxypropylene (PEO-PPO) block copolymers. When such a material is used, it can be delivered to the calyx 34 in liquid form, and then transition into a gel as it is heated by the kidney 10. Alternative temperature-sensitive materials include those that are in liquid form at or above normal body temperature, but form a gel below body temperature. In such a case, the material can be deposited within the calyx 34 and cooled to form a gel. Examples of such materials include gelatin materials.

In other embodiments, the marking material 36 comprises two separate component that, when mixed, form a gel. One example of such materials are those that include crosslinkable polymers that form a gel when contacted with a crosslinking agent. Crosslinkable polymers that may be suitable for use in the invention include both ionically crosslinkable and non-ionically crosslinkable polymers. Crosslinking agents that may be employed include both ionic crosslinking agents and non-ionic crosslinking agents. Ionically crosslinkable polymers include anionic crosslinkable polymers and cationic crosslinkable polymers that may be used in conjunction with anionic crosslinking agents and cationic crosslinking agents, respectively.

Irrespective of the type of marking material 36 that is used, the marking material is a temporary implant that it is automatically or manually removed once it is no longer needed to identify the calyx 34 (or other cavity). For example, in cases in which the marking material 36 is a temperature-sensitive material, the material will slowly degrade within the kidney and be excreted. Optionally, the speed with which the temperature-sensitive gel breaks down can be increased by either cooling or heating the marking material 36, depending upon whether the material forms a gel at higher or lower temperatures.

In cases in which the marking material 36 comprises two separate components that together form a gel, breakdown of the marking material can, for example, be achieved by providing a third material that degrades the gel. For instance, if the marking material 36 includes a crosslinkable polymer, a suitable de-crosslinking agent may be used to dissolve the gel, in which case the material will again be excreted. Suitable de-crosslinking agents include sodium phosphate, sodium citrate, inorganic sulfates, ethylene diamine tetraacetic acid and ethylene dime tetraacetate, citrates, organic phosphates (e.g., cellulose phosphate), inorganic phosphates (e.g., pentasodium tripolyphosphate, mono- and di-basic potassium phosphate, sodium pyrophosphate), phosphoric acid, trisodium carboxymethyloxy succinate, nitrilotriacetic acid, maleic acid, oxalate, polyacrylic acid, sodium, potassium, calcium, or magnesium ions.

In still other embodiments, the gel may be removed by drawing the gel out of the calyx using a lumen of the viewing device or a separate catheter.

Although the marking material 36 may, in some cases, naturally degrade and be excreted over time, the marking material will remain in place for at least the duration of the inspection procedure. Therefore, as the surgeon moves on to other calices 16 (or other cavities), the marking material 36 will continue to provide a visual marker of where the surgeon has already been.

Figure 2C:
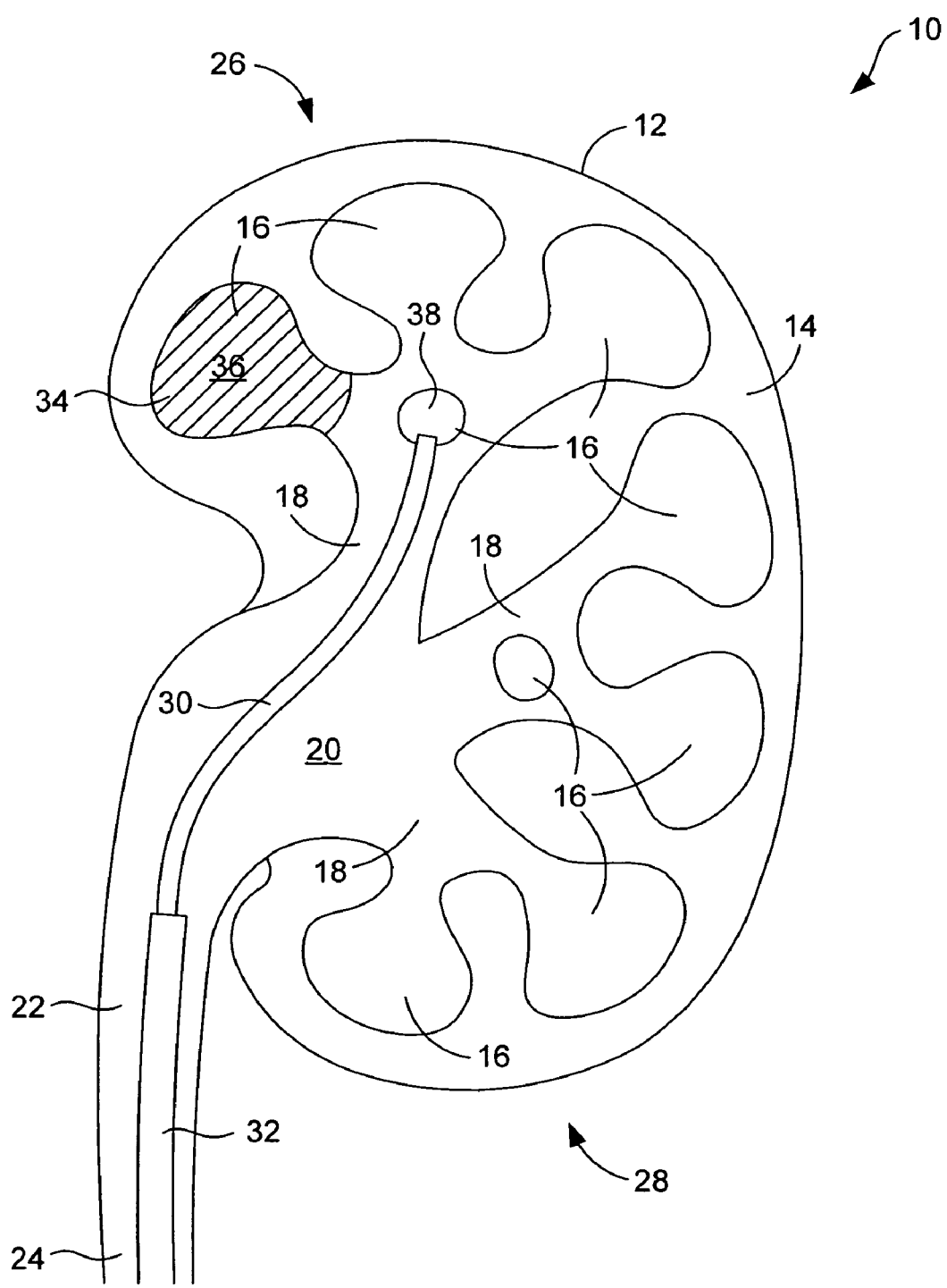
FIG. 2C is a schematic cross-sectional view of a kidney, illustrating inspection of a second calyx using a viewing device.
Figure 2D:
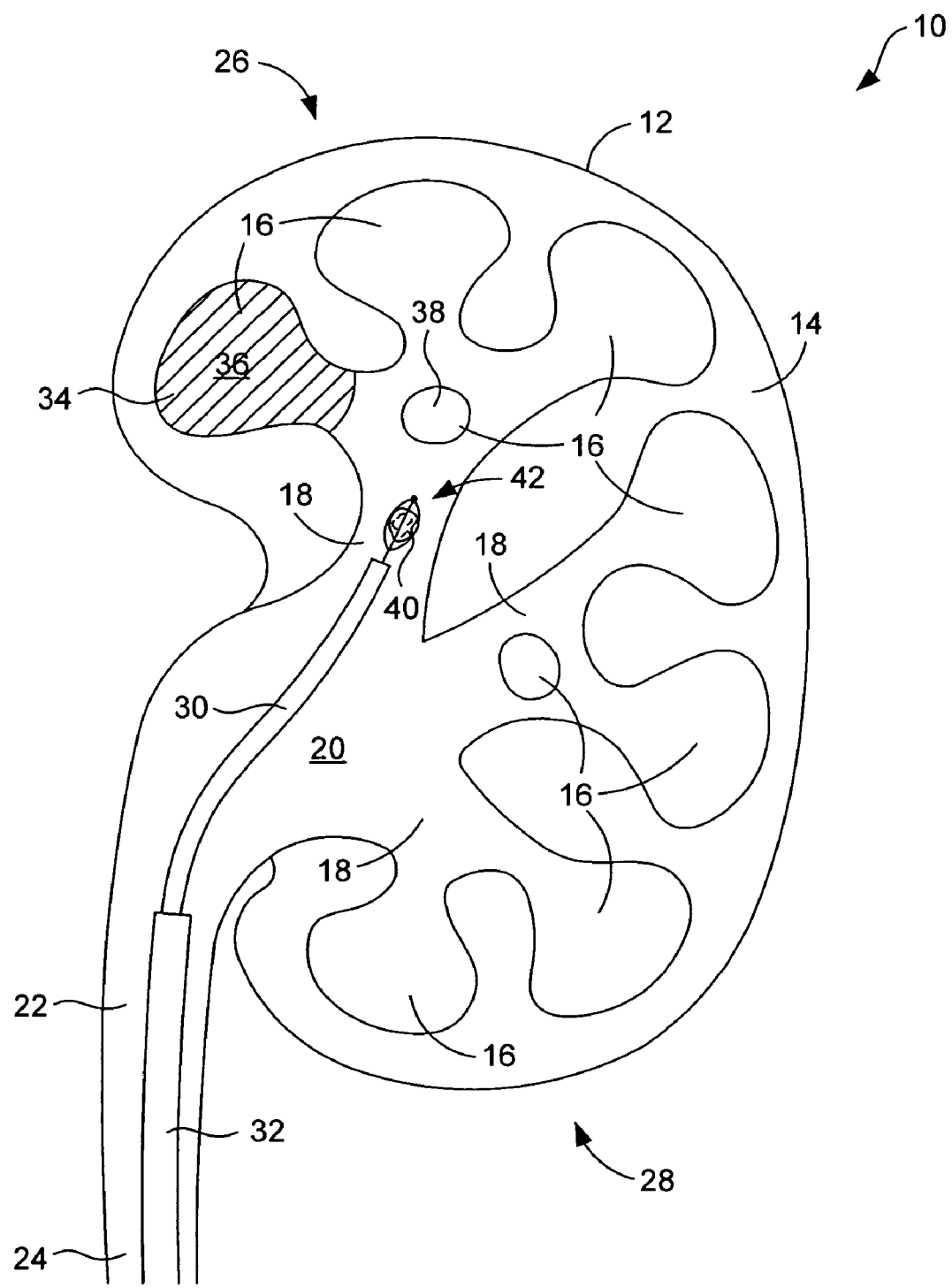
FIG. 2D is a schematic cross-sectional view of a kidney, illustrating removal of a stone from the second calyx using a retrieval device.

Referring now to FIG. 2C, the surgeon has manipulated the viewing device 30 such that it is positioned for insertion into a second calyx 38 (which extends into the page in FIG. 2C). Assuming that the second calyx 38 comprises a stone (not visible in FIG. 2C), the surgeon can identify the stone using the viewing device 30, and then remove it. Referring to FIG. 2D, the surgeon has removed the stone 40 using a retrieval device 42. By way of example, the retrieval device 42 is inserted through a working channel of the viewing device 30. In such a case, the retrieval device 42 and the viewing device 30 can be withdrawn from the body together (e.g., via the access sheath 32) to remove the stone 40. Alternatively, the retrieval device 42 can be inserted into the kidney 10 separate from the viewing device 30.

Figure 2E:
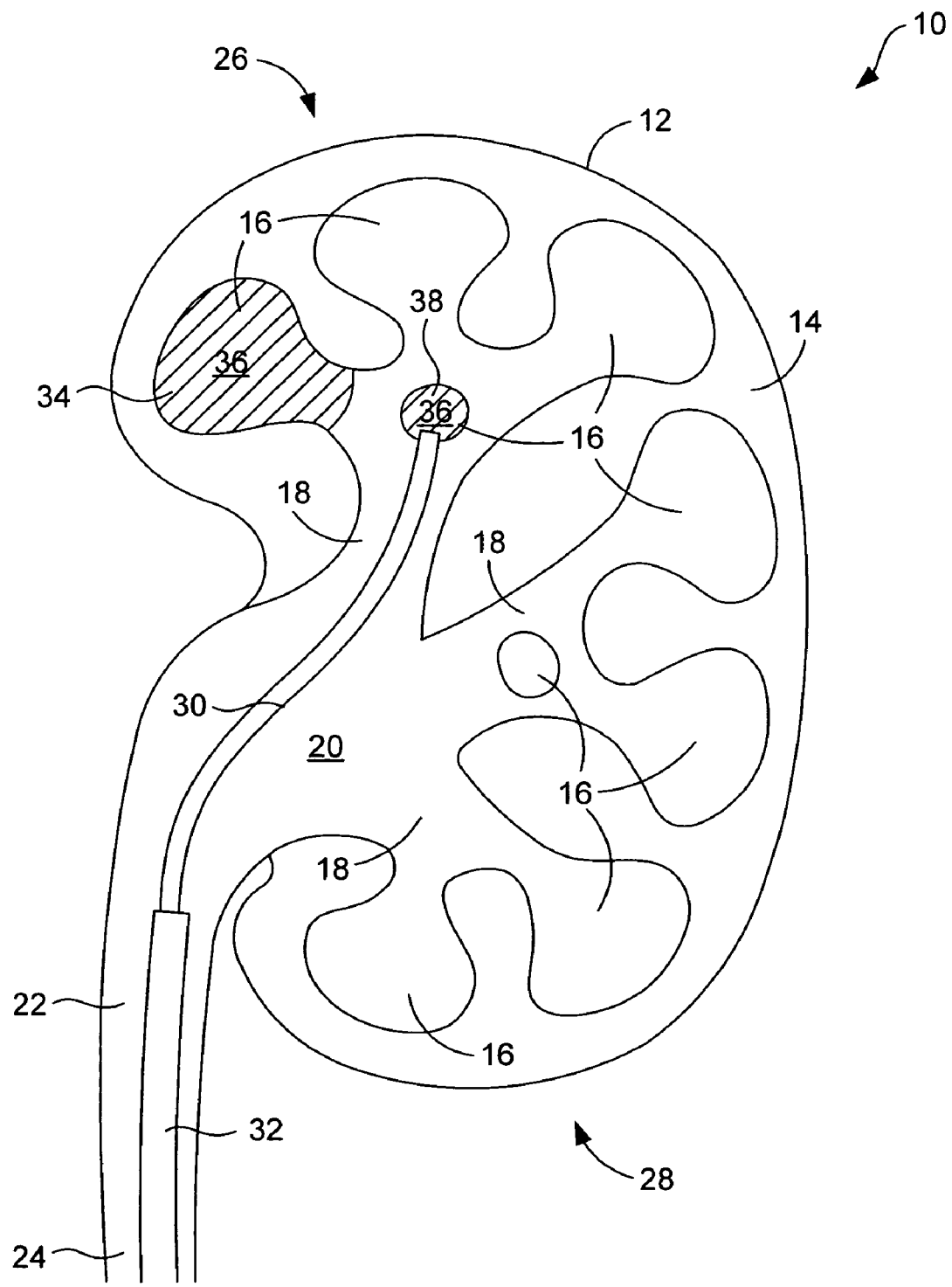
FIG. 2E is a schematic cross-sectional view of a kidney, illustrating marking the second calyx with a marking material.

After the stone 40 has been removed, and assuming no other stones exist in the second calyx 38, the calyx can be marked with the marking material 36 in similar manner to that described above in relation to the first calyx 34. Accordingly, the second calyx 38 can, for example, be filled with the marking material 36 as is indicated in FIG. 2E. Again, such filling can be accomplished using a working or irrigation channel of the viewing device 30, a separate catheter, or a percutaneous injection device.

The above-described process can continue in similar manner until every calyx 16 has been inspected, all stones have been removed, and all inspected calices have been marked. In such a case, the surgeon can readily determine that each calyx has been inspected. In cases in which the marking material 36 comprises a gel, a further benefit is provided if lithotripsy is performed. Specifically, once a calyx 16, or its entrance, has been filled with a gel-based marking material, fragments that break off of a stone during lithotripsy will not be able to enter the calyx. Therefore, the surgeon need not recheck previously-inspected calices after lithotripsy.

Figure 3A:
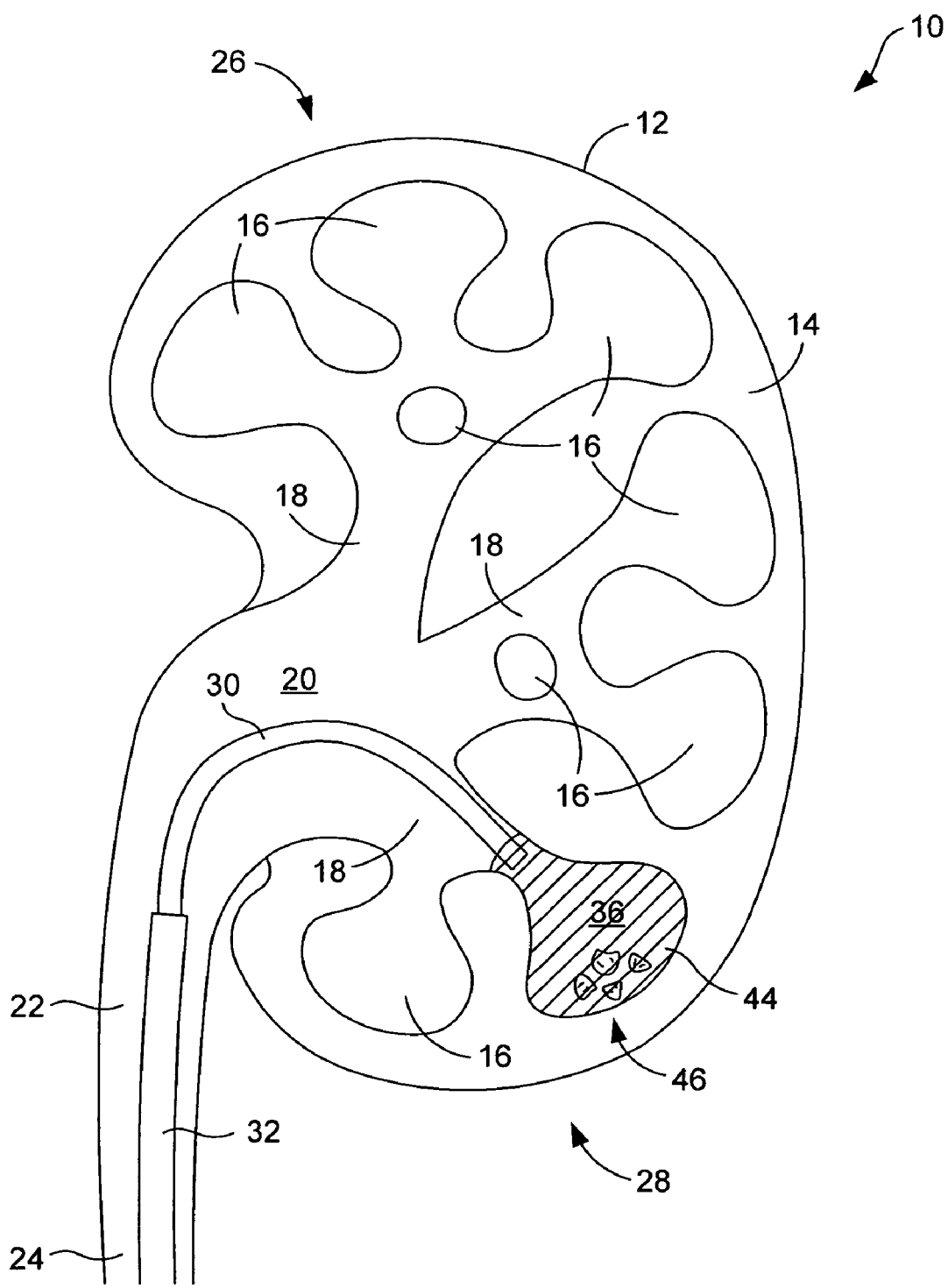
FIG. 3A is a schematic cross-sectional view of a kidney, illustrating marking a third calyx with a marking material.
Figure 3B:
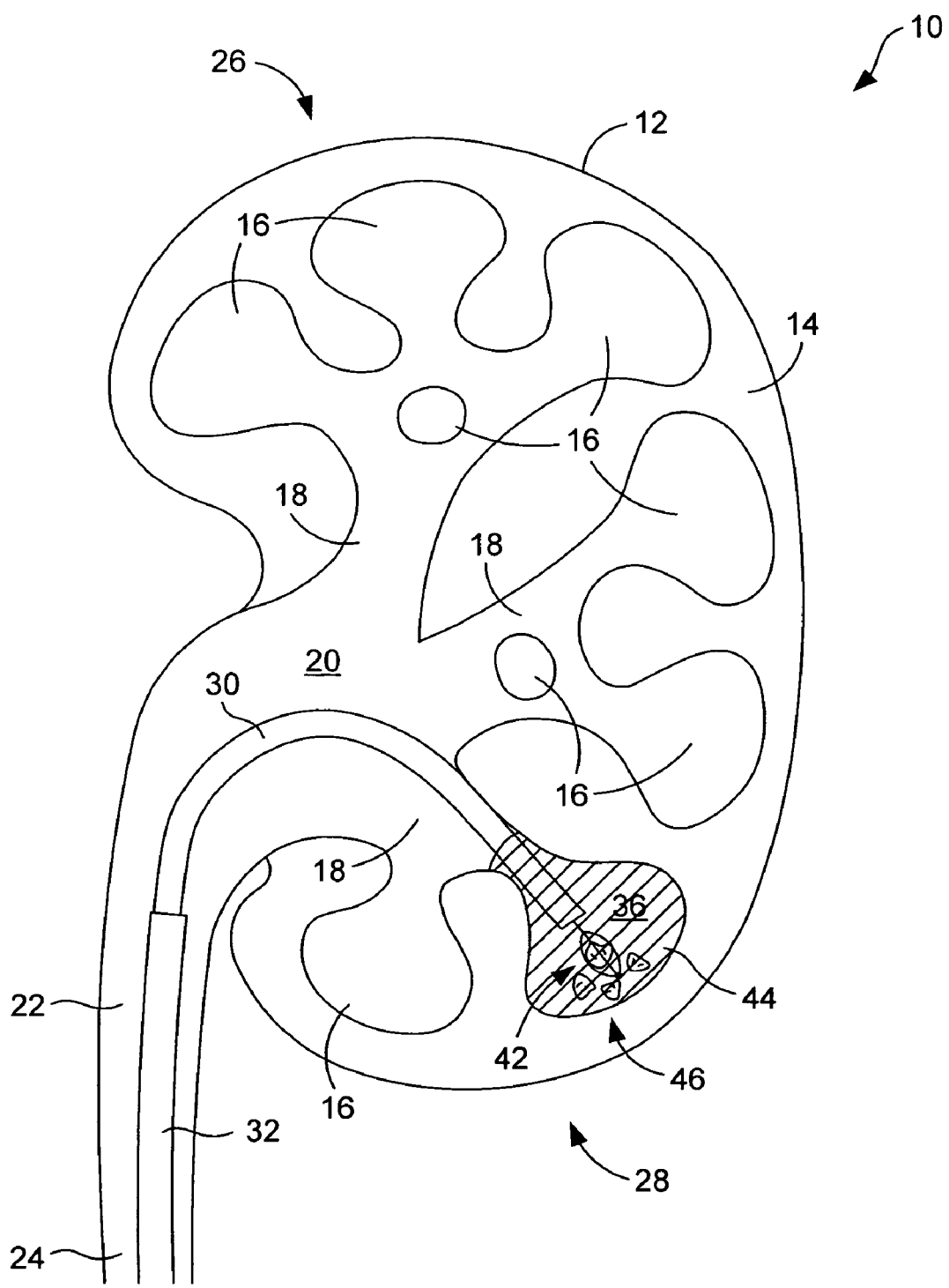
FIG. 3B is a schematic cross-sectional view of a kidney, illustrating removal of a stone from the third calyx using a retrieval device.

FIGS. 3A and 3B illustrate an example of a further marking application. Beginning with FIG. 3A, a given calyx 44 comprises a plurality of stones 46 that are to be removed. By way of example, the stones 46 comprise fragments of a larger stone that was broken up through lithotripsy. Assuming that the surgeon can only remove one stone 46 at a time, or at least cannot remove all of the stones at once, the surgeon may need to return to the calyx 44 one or more times after withdrawing the viewing device 30. In such a case, it may be difficult for the surgeon to relocate the calyx 44 or distinguish it from other calices 16 of the kidney 10. To aid the surgeon in such relocation, the surgeon can mark the calyx 44 with the marking material 36, as is indicated in FIG. 3A. After marking the calyx 44, the surgeon can then remove the stones 46 (e.g., one by one) from the calyx through the marking material 36 using the retrieval device 42. In cases in which the marking material 36 is a gel, the marking material will stay in place despite the insertion and withdrawal of the viewing device 30 and/or retrieval device 42.

Figure 4:
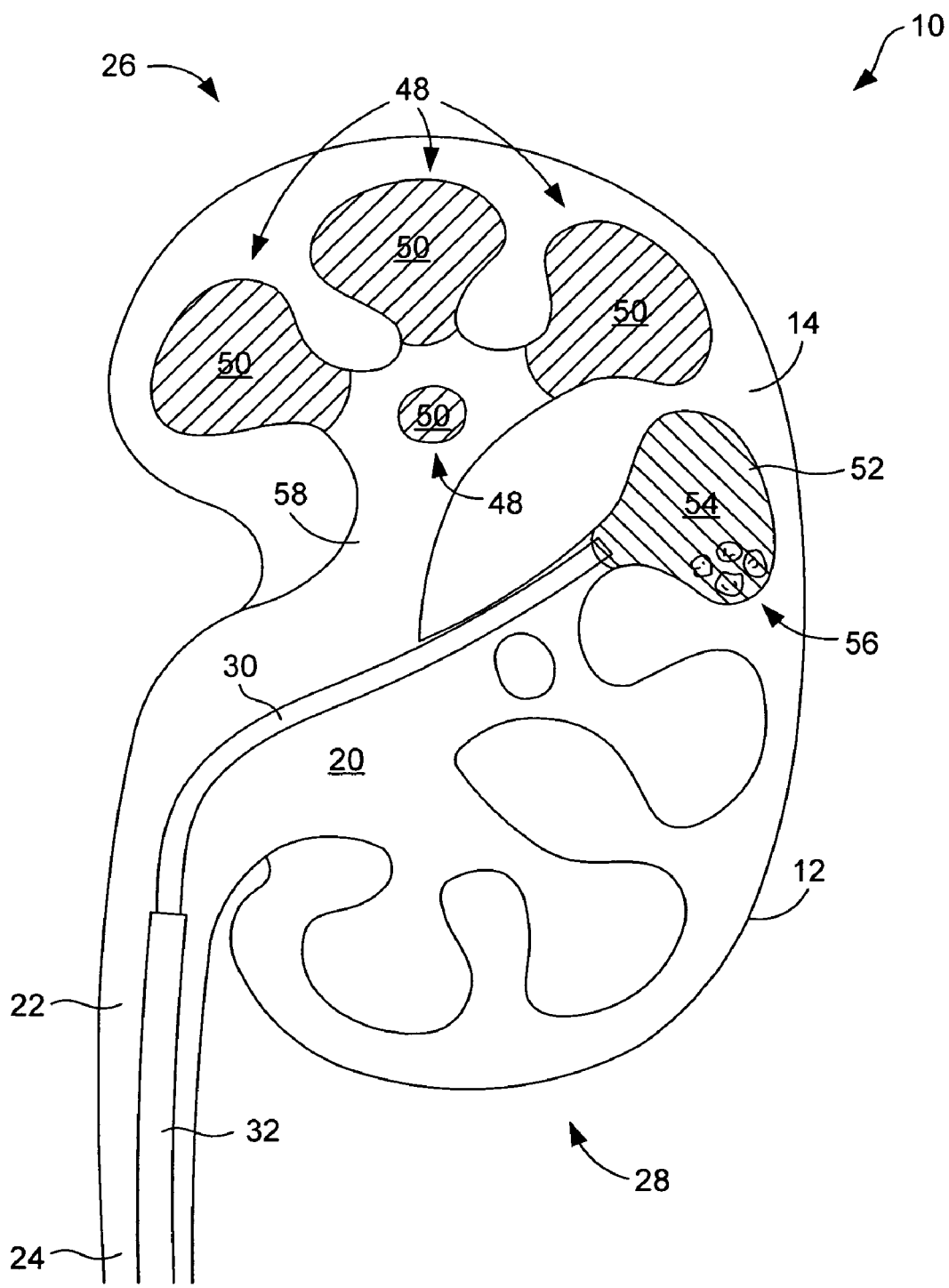
FIG. 4 is a schematic cross-sectional view of a kidney, illustrating filling of a group of calices with a first marking material, and filing a separate calyx with a second marking material.

FIG. 4 illustrates a further marking application. In this application, several of the calices 48 have been marked with a first marking material 50 to indicate a first condition, and one calyx 52 has been marked with a second marking material 54 to indicated a second condition. In this example, the first condition is absence of any stones and the second condition is presence of one or more stones 56. The marking material 50 is distinguishable from the marking material 54 in one or more ways. In some embodiments, the marking material 50 comprises a different colored dye than the marking material 54 comprises. In such a case, the surgeon can distinguish the two types of calices (e.g., those containing stones and those not containing stones) using the viewing device 30. In addition or exception, the marking material 50 comprises a different concentration of contrast agent than the marking material 54. In such a case, the surgeon can distinguish the two types of calices from a fluoroscopic image.

As is indicated in FIG. 4, each of the calices 48 extends from a major calyx 58. In such a case, in which the cavities to be marked comprise all of the cavities of a given group or branch of cavities, the entire calyx 58 can be filled with the marking material 50 to indicate that that entire portion of the kidney 10 has already been inspected.

The invention claimed is:

1. A method for marking regions of a kidney comprising:
   inserting an internal viewing device via a ureter into a first calyx of the kidney;
   inspecting the first calyx using the internal viewing device to detect the presence of one or more objects to be removed;
   marking the first calyx, based on the inspection, with a marking material to provide a visual indication regarding the results of the inspection; and
   moving the internal viewing device from the first calyx to a second calyx of the kidney for subsequent inspecting and marking thereof, wherein the marking of the first calyx and the second calyx comprises marking with a first marking material when the inspection indicates the presence of objects to be removed and marking with a second marking material different from the first marking material when the inspection indicates no presence of objects to be removed.

2. The method of claim 1, wherein the internal viewing device comprises an endoscope or ureteroscope.

3. The method of claim 1, wherein marking the first calyx comprises depositing the marking material in the first calyx.

4. The method of claim 3, wherein depositing the marking material in the first calyx comprises filling the entire first calyx.

5. The method of claim 3, wherein depositing the marking material in the first calyx comprises filling only an entrance to the first calyx.

6. The method of claim 5, wherein the marking material used to fill the entrance of the first calyx prevents objects from other calyces from entering the first calyx.

7. The method of claim 1, wherein the marking material comprises a contrast agent.

8. The method of claim 1, wherein the marking material is colored.

9. The method of claim 1, further comprising the step of marking other calyces of the kidney with either the first type of marking material or the second type of marking material depending on the presence of one or more objects to be removed therefrom.

10. The method of claim 1, wherein the first calyx contains more than one object to be removed, and wherein the marking step provides a visual indication of the presence of more than one object.

11. The method of claim 1, further comprising marking each calyx of the kidney with a marking material based on the respective inspection thereof.

12. The method of claim 11, further comprising removing one or more objects from each calyx of the kidney that contains one or more objects to be removed.

* * * * *